(12) United States Patent
Butscher et al.

(10) Patent No.: US 9,907,654 B2
(45) Date of Patent: Mar. 6, 2018

(54) BONE SUBSTITUTE AND METHOD FOR PRODUCING THE SAME

(71) Applicant: Dr. H.C. Robert Mathys Stiftung, Bettlach (CH)

(72) Inventors: Andre Butscher, Lüterkofen (CH); Marc Bohner, Grenchen (CH); Nicola Döbelin, Solothurn (CH)

(73) Assignee: Dr. H.C. Robert Mathys Stiftung, Bettlach (CH)

( * ) Notice: Subject to any disclaimer, the term of this patent is extended or adjusted under 35 U.S.C. 154(b) by 0 days.

(21) Appl. No.: 14/650,495

(22) PCT Filed: Dec. 11, 2012

(86) PCT No.: PCT/CH2012/000270
§ 371 (c)(1),
(2) Date: Jun. 8, 2015

(87) PCT Pub. No.: WO2014/089711
PCT Pub. Date: Jun. 19, 2014

(65) Prior Publication Data
US 2015/0297349 A1    Oct. 22, 2015

(51) Int. Cl.
*A61F 2/28*    (2006.01)
*A61L 27/12*    (2006.01)
(Continued)

(52) U.S. Cl.
CPC ............ *A61F 2/28* (2013.01); *A61L 27/12* (2013.01); *B29C 64/165* (2017.08);
(Continued)

(58) Field of Classification Search
CPC ........ A61F 2/28; A61F 2/2803; A61F 2/2814; A61F 2002/2807; A61F 2002/281;
(Continued)

(56) References Cited

U.S. PATENT DOCUMENTS 3,852,045 A * 12/1974 Wheeler .................. A61F 2/28
419/2
5,152,791 A * 10/1992 Hakamatsuka ........... A61F 2/28
623/23.56
(Continued)

FOREIGN PATENT DOCUMENTS

WO    95/11007 A1    4/1995
WO    02/083194 A1    10/2002
(Continued)

*Primary Examiner* — Alvin Stewart
(74) *Attorney, Agent, or Firm* — Rankin, Hill & Clark LLP

(57) ABSTRACT

The invention relates to a bone substitute (1) comprising A) a container (2) made of a porous casing (4) which is at least partly provided with openings; and B) a plurality of filler elements (5) which are not connected to one another and which are enclosed in the container (2); wherein C) the filler elements (5) consist of interconnected particles with an average diameter $D_P$; and D) the openings of the casing (4) are interconnected pores or channels with an average diameter of $D_M$.

29 Claims, 6 Drawing Sheets

(51) Int. Cl.
 *B29C 64/165* (2017.01)
 *A61F 2/30* (2006.01)
 *B33Y 10/00* (2015.01)
 *B33Y 70/00* (2015.01)
 *B33Y 80/00* (2015.01)
 *B29L 31/00* (2006.01)

(52) U.S. Cl.
 CPC ... *A61F 2/3094* (2013.01); *A61F 2002/30011* (2013.01); *A61F 2002/30199* (2013.01); *A61F 2002/30224* (2013.01); *A61F 2002/30588* (2013.01); *A61F 2002/30784* (2013.01); *A61F 2002/30968* (2013.01); *A61F 2210/0076* (2013.01); *A61F 2310/00293* (2013.01); *A61L 2430/02* (2013.01); *B29L 2031/7532* (2013.01); *B33Y 10/00* (2014.12); *B33Y 70/00* (2014.12); *B33Y 80/00* (2014.12)

(58) Field of Classification Search
 CPC ...... A61F 2002/2835; A61F 2002/2839; A61F 2002/2842; A61F 2002/2846; A61F 2002/285; A61F 2002/2875; A61F 2002/30004; A61F 2002/30006; A61F 2002/30011; A61L 27/12
 USPC ............. 623/23.61, 23.75, 23.55, 23.72
 See application file for complete search history.

(56) References Cited

U.S. PATENT DOCUMENTS

| | | | | |
|---|---|---|---|---|
| 5,192,326 | A * | 3/1993 | Bao | A61F 2/441 623/17.12 |
| 5,282,861 | A * | 2/1994 | Kaplan | A61F 2/28 427/2.26 |
| 5,348,788 | A * | 9/1994 | White | A61F 2/0077 428/131 |
| 5,496,372 | A * | 3/1996 | Hamamoto | A61C 8/0012 606/298 |
| 5,876,452 | A * | 3/1999 | Athanasiou | A61F 2/28 424/424 |
| 5,888,220 | A * | 3/1999 | Felt | A61B 17/7097 128/898 |
| 5,906,616 | A * | 5/1999 | Pavlov | A61B 17/862 606/247 |
| 6,013,853 | A * | 1/2000 | Athanasiou | A61F 2/0811 424/423 |
| 6,022,376 | A * | 2/2000 | Assell | A61F 2/441 623/17.12 |
| 6,149,650 | A * | 11/2000 | Michelson | A61B 17/1671 623/17.16 |
| 6,187,043 | B1 * | 2/2001 | Ledergerber | A61F 2/0077 623/11.11 |
| 6,187,329 | B1 * | 2/2001 | Agrawal | A61F 2/28 424/424 |
| 6,283,997 | B1 * | 9/2001 | Garg | A61F 2/28 623/16.11 |
| 6,454,811 | B1 * | 9/2002 | Sherwood | A61F 2/28 623/23.72 |
| 6,520,997 | B1 * | 2/2003 | Pekkarinen | A61F 2/00 623/23.72 |
| 6,869,445 | B1 * | 3/2005 | Johnson | A61F 2/28 623/16.11 |
| 7,189,263 | B2 * | 3/2007 | Erbe | A61B 17/80 424/422 |
| 7,442,303 | B2 * | 10/2008 | Jacobson | B01D 63/16 210/500.22 |
| 7,465,318 | B2 * | 12/2008 | Sennett | A61B 17/7098 606/92 |
| 7,503,933 | B2 * | 3/2009 | Michelson | A61F 2/30744 623/17.11 |
| 7,632,228 | B2 * | 12/2009 | Brauker | A61B 5/076 204/403.07 |
| 7,837,735 | B2 * | 11/2010 | Malone | A61B 17/7064 623/17.16 |
| 7,901,462 | B2 * | 3/2011 | Yang | A61C 8/0012 623/23.76 |
| 8,012,211 | B2 * | 9/2011 | Kuslich | A61F 2/442 623/17.12 |
| 8,372,423 | B2 * | 2/2013 | Marshall | A61L 27/56 424/400 |
| 8,414,654 | B1 * | 4/2013 | Ganey | A61F 2/28 623/16.11 |
| 8,636,803 | B2 * | 1/2014 | Hibri | A61F 2/441 623/17.12 |
| 8,702,808 | B2 * | 4/2014 | Teoh | 623/23.61 |
| 8,927,022 | B2 * | 1/2015 | Maginness | A61L 27/52 424/489 |
| 8,932,309 | B2 * | 1/2015 | Linares | A61L 27/56 606/151 |
| 9,289,312 | B2 * | 3/2016 | Davenport | A61L 27/042 |
| 9,327,056 | B2 * | 5/2016 | Bandyopadhyay | A61L 27/56 |
| 2002/0035401 | A1 * | 3/2002 | Boyce | A61F 2/28 623/23.51 |
| 2002/0077701 | A1 * | 6/2002 | Kuslich | A61F 2/441 623/17.12 |
| 2002/0116064 | A1 * | 8/2002 | Middleton | A61F 2/446 623/17.16 |
| 2002/0147497 | A1 * | 10/2002 | Belef | A61F 2/02 623/17.12 |
| 2002/0169066 | A1 * | 11/2002 | Cassidy | A61F 2/28 501/80 |
| 2002/0183848 | A1 * | 12/2002 | Ray | A61F 2/441 623/17.12 |
| 2003/0004578 | A1 * | 1/2003 | Brown | B29C 44/1214 623/23.72 |
| 2003/0012805 | A1 * | 1/2003 | Chen | A61F 2/30756 424/423 |
| 2003/0036797 | A1 * | 2/2003 | Malaviya | A61B 17/064 623/14.12 |
| 2003/0114854 | A1 * | 6/2003 | Pavlov | A61B 17/862 606/249 |
| 2003/0125739 | A1 * | 7/2003 | Bagga | A61F 2/4455 606/247 |
| 2004/0191106 | A1 * | 9/2004 | O'Neill | A61F 2/30907 419/2 |
| 2004/0249464 | A1 * | 12/2004 | Bindseil | A61F 2/4455 623/17.16 |
| 2004/0249471 | A1 * | 12/2004 | Bindseil | A61F 2/4455 623/23.51 |
| 2005/0021151 | A1 * | 1/2005 | Landis | A61F 2/28 623/23.63 |
| 2005/0043816 | A1 * | 2/2005 | Datta | A61L 27/18 623/23.61 |
| 2005/0102036 | A1 * | 5/2005 | Bartee | A61C 8/0006 623/23.76 |
| 2005/0112397 | A1 * | 5/2005 | Rolfe | A61B 17/8605 428/593 |
| 2005/0113934 | A1 * | 5/2005 | Kim | A61F 2/30767 623/23.56 |
| 2005/0251259 | A1 * | 11/2005 | Suddaby | A61F 2/441 623/17.12 |
| 2005/0278027 | A1 * | 12/2005 | Hyde, Jr. | A61F 2/442 623/17.12 |
| 2006/0106461 | A1 * | 5/2006 | Embry | A61B 17/7097 623/17.12 |
| 2006/0149379 | A1 * | 7/2006 | Kuslich | A61B 17/68 623/17.12 |
| 2006/0206209 | A1 * | 9/2006 | Cragg | A61B 17/8811 623/17.16 |
| 2006/0229735 | A1 * | 10/2006 | Roy | A61F 2/0077 623/23.74 |
| 2006/0241756 | A1 * | 10/2006 | Fritz | C12N 5/0655 623/14.12 |
| 2007/0113951 | A1 * | 5/2007 | Huang | A61F 2/30756 156/89.11 |
| 2007/0116734 | A1 * | 5/2007 | Akash | A61F 2/30 424/423 |

(56) References Cited

U.S. PATENT DOCUMENTS

| | | | | |
|---|---|---|---|---|
| 2007/0135921 A1* | 6/2007 | Park | A61F 2/441 | 623/17.12 |
| 2007/0142914 A1* | 6/2007 | Jones | A61F 2/30907 | 623/14.13 |
| 2007/0173940 A1* | 7/2007 | Hestad | A61F 2/44 | 623/17.12 |
| 2007/0233258 A1* | 10/2007 | Hestad | A61B 17/7098 | 623/17.12 |
| 2008/0188945 A1* | 8/2008 | Boyce | A61B 17/0401 | 623/23.61 |
| 2008/0195210 A1* | 8/2008 | Milijasevic | A61F 2/441 | 623/17.16 |
| 2008/0249632 A1* | 10/2008 | Stone | A61F 2/28 | 623/23.5 |
| 2008/0281431 A1* | 11/2008 | Missos | A61F 2/28 | 623/23.56 |
| 2009/0024224 A1* | 1/2009 | Chen | A61B 17/1604 | 623/23.72 |
| 2009/0043398 A1* | 2/2009 | Yakimicki | B29C 41/06 | 623/23.51 |
| 2009/0157194 A1* | 6/2009 | Shikinami | A61B 17/8625 | 623/23.72 |
| 2009/0187249 A1* | 7/2009 | Osman | A61B 17/7097 | 623/17.16 |
| 2009/0317447 A1* | 12/2009 | Hsiao | A61F 2/28 | 424/426 |
| 2010/0009103 A1* | 1/2010 | Kuboki | A61F 2/28 | 428/34.6 |
| 2010/0021520 A1* | 1/2010 | Baskin | A61L 27/58 | 424/423 |
| 2010/0137990 A1* | 6/2010 | Apatsidis | A61L 27/56 | 623/17.16 |
| 2010/0145454 A1* | 6/2010 | Hoffman | A61F 2/447 | 623/17.12 |
| 2010/0256758 A1* | 10/2010 | Gordon | A61F 2/30756 | 623/16.11 |
| 2010/0268337 A1* | 10/2010 | Gordon | A61F 2/30756 | 623/16.11 |
| 2010/0278891 A1* | 11/2010 | Ringeisen | A61B 17/80 | 424/422 |
| 2010/0292146 A1* | 11/2010 | Seibl | A61F 2/28 | 514/8.8 |
| 2010/0310623 A1* | 12/2010 | Laurencin | A61F 2/28 | 424/423 |
| 2010/0331998 A1* | 12/2010 | Ringeisen | A61F 2/28 | 623/23.61 |
| 2011/0004307 A1* | 1/2011 | Ahn | A61F 2/441 | 623/17.12 |
| 2011/0009979 A1* | 1/2011 | Shaw | B23K 1/0008 | 623/23.53 |
| 2011/0054408 A1* | 3/2011 | Wei | A61B 17/68 | 604/175 |
| 2011/0054615 A1* | 3/2011 | Buckland | A61L 27/12 | 623/17.11 |
| 2011/0071635 A1* | 3/2011 | Zhang | B32B 15/08 | 623/17.11 |
| 2011/0118850 A1* | 5/2011 | Govil | A61F 2/4644 | 623/23.61 |
| 2011/0125284 A1* | 5/2011 | Gabbrielli | A61F 2/30767 | 623/23.4 |
| 2011/0245930 A1* | 10/2011 | Alley | A61F 2/3094 | 623/23.74 |
| 2011/0282392 A1* | 11/2011 | Murphy | A61K 38/30 | 606/279 |
| 2011/0307073 A1* | 12/2011 | Teoh | A61F 2/28 | 623/23.61 |
| 2011/0313538 A1* | 12/2011 | Oh | A61L 27/56 | 623/23.61 |
| 2012/0065739 A1* | 3/2012 | Grohowski, Jr. | A61F 2/30767 | 623/23.53 |
| 2012/0116515 A1* | 5/2012 | Semler | A61B 17/7095 | 623/17.16 |
| 2012/0150299 A1* | 6/2012 | Ergun | B29C 47/6037 | 623/17.11 |
| 2012/0251609 A1* | 10/2012 | Huang | A61L 27/3608 | 424/423 |
| 2012/0253474 A1* | 10/2012 | Klein | A61F 2/28 | 623/23.76 |
| 2012/0330435 A1* | 12/2012 | Engqvist | A61B 17/8085 | 623/23.61 |
| 2013/0123935 A1* | 5/2013 | Hunt | A61F 2/28 | 623/23.61 |
| 2013/0173013 A1* | 7/2013 | Anderson | A61F 2/28 | 623/23.61 |
| 2013/0211533 A1* | 8/2013 | Fonte | A61L 27/00 | 623/22.4 |
| 2013/0274890 A1* | 10/2013 | McKay | A61F 2/4455 | 623/23.5 |
| 2013/0310948 A1* | 11/2013 | Luscher | A61B 17/68 | 623/23.58 |
| 2013/0325129 A1* | 12/2013 | Huang | A61F 2/44 | 623/17.16 |
| 2013/0325142 A1* | 12/2013 | Hunter | C22C 1/08 | 623/23.51 |
| 2014/0025181 A1* | 1/2014 | Vanasse | A61F 2/28 | 623/23.55 |
| 2014/0088716 A1* | 3/2014 | Zubok | A61F 2/3094 | 623/18.11 |
| 2014/0107786 A1* | 4/2014 | Geisler | A61F 2/30965 | 623/17.16 |
| 2014/0264995 A1* | 9/2014 | Lakshminarayanan | A61F 2/442 | 264/54 |
| 2014/0277461 A1* | 9/2014 | Nebosky | A61F 2/44 | 623/17.11 |
| 2014/0277491 A1* | 9/2014 | Fang | A61F 2/4455 | 623/17.16 |
| 2014/0277580 A1* | 9/2014 | Knapp | A61F 2/852 | 623/23.74 |
| 2015/0018968 A1* | 1/2015 | Sun | A61L 27/38 | 623/23.74 |
| 2015/0045903 A1* | 2/2015 | Neal | B23K 15/0006 | 623/21.18 |
| 2015/0150681 A1* | 6/2015 | Ricci | A61L 27/54 | 623/23.51 |
| 2016/0128837 A1* | 5/2016 | Juszczyk | A61F 2/30756 | 623/18.11 |
| 2016/0184103 A1* | 6/2016 | Fonte | A61L 27/306 | 623/23.5 |

FOREIGN PATENT DOCUMENTS

| | | |
|---|---|---|
| WO | 2008/082766 A2 | 7/2008 |
| WO | 2011/022550 A1 | 2/2011 |

* cited by examiner

BONE SUBSTITUTE AND METHOD FOR PRODUCING THE SAME

The invention relates to a bone substitute, and to a method for producing the same.

Conventional production methods for producing bone substitute materials are known from the prior art which cannot completely control the porosity and also the geometry. Such production methods include, e.g., templating, emulsion methods, lost wax method. In particular, the geometry can be determined by these methods typically only in a limited range by the mold, for example. Thus, the outer edge of the geometry cannot be arbitrarily complex due to the required releasability. In particular, however, the internal geometry or architecture of the bone substitute material can be determined only via the porosity. It is limited by the geometry and arrangement of the pore fillers. Furthermore, for the formation of pores pore fillers are needed, which can lead to undesired interactions. Typically, only sphere-like pores can be produced. In addition to the limited pore geometry, the pore density or distribution within the bone substitute material is difficult to control. It would be desirable, therefore, to obtain a bone substitute, wherein the porosity specifically in the inner core of the supporting matrix or scaffold has a greater porosity than the edge region. Typically, however, it is just the opposite in the conventional methods, with the result that cell/scaffold interactions focus on the edge region.

The invention aims to remedy this situation. The object of the invention is to provide a bone substitute, which:
a) has a complex geometry with high porosity also in the interior;
(in the known methods of the prior art, the internal geometry is not freely controllable by the geometry and arrangement of pore fillers. In the conventional SFF methods (Solid Freeform Fabrication) such as 3DP and SLS, which are used for the method according to the invention channels having a geometry that cannot be chosen freely must be generated in the interior to enable removal of loose powder. The invention aims to remedy this situation and enables an interior architecture, which is not feasible with conventional SFF methods)
b) allows the migration of cells;
c) has an optimal surface to volume ratio, wherein per volume a surface as large as possible is available that is accessible for the bone cells;
d) has a strength which allows the manipulation that is typically necessary of the bone substitute without damage;
e) gets by with very little or no polymer components;
(thus, there are no toxic components, e.g., remaining monomers and crosslinkers, there is no degradation during sterilization, problematic degradation products, such as, e.g., acids are avoided and there is no reduction in the rate of degradation.)
f) enables a simple "depowdering" even of complex geometries inside the container through the freely moving filler elements and
g) is simple and inexpensive to produce.

The invention solves this problem with a bone substitute as disclosed and claimed herein, and with a method for producing the same as disclosed and claimed herein.

Further advantageous embodiments of the invention can be commented as follows:

In a specific embodiment, the container has one or more windows passing through the casing. Thus, the loose particles can be removed from the cavity of the container through the window(s) by depowdering.

In another embodiment, the dimensions of the individual filler elements are defined by the longest enveloping circular cylinder of the diameter $D_z$.

In another embodiment, the average diameter $D_P$ of the particles is between 1 μm and 250 μm.

In another embodiment, the average diameter $D_M$ of the pores or channels is less than $D_z$. In another embodiment, each of the windows has a smallest dimension $D_F$ which is governed by the formula $D_Z > D_F > D_P$.

In yet another embodiment, the diameter $D_Z$ is larger than 200 μm, preferably larger than 500 μm.

In a further embodiment, the diameter $D_F$ is larger than 50 μm.

In another embodiment, the filler elements and the casing are produced in one operation by means of a three-dimensional printing method, 3DP, or a selective laser-sintering method, SLS. Alternatively, the bone substitute according to the invention can be produced by producing a hollow cylinder, filling the cylinder with small particles and closing the ends of the cylinder with a hydraulic cement.

In another embodiment, the filler elements are spaced apart from one another, wherein preferably the minimal distance between the filler elements is larger than 50 μm. If the fillers are placed too close together, they can stick together.

In another embodiment, the casing contains, in addition to the openings and the windows, a number of passages having a diameter $D_D$ which is at least equal in size to $D_P$ and is at least 30 μm.

In a further embodiment, the casing has interparticle and intercrystalline interstices with an average diameter which is in the range of $0.1 \, D_P$ to $0.5 \, D_P$, and is 1 to 50 μm.

In still another embodiment, the casing of the container and the filler elements are the reaction product of the solidification of a loose powder of the particles, preferably produced by means of 3DP or SLS.

EXAMPLES a) solidification by crystal formation or polymerization (e.g., sugar or salt powder+water from the print head or as a further alternative, any powder+salt/sugar/polymer solution from the print head).
   Example: sugar/CaP powder bed is sprayed locally with water droplets (from the print head via 3DP). Interlocking of the sugar crystals forms a matrix which holds together the CaP particles. Subsequent steps could include a further composite of CaP or washing out of the sugar crystals.
b) solidification by capillary forces: drying and interlocking of the surface of a powder;
c) solidification by gelation (e.g. alginate+$Ca^{2+}$ ions=gel)
   Example: cellulose powder is dissolved and solidified locally by a suitable printed solution;
d) solidification by cooling (e.g., a liquid medium is printed on a powder and solidifies by cooling);
   Example: polymer solution printed on powder bed of any material.
e) solidification by sintering or melting and cooling (SLS or SLM (Selective Laser Melting) method).

In another embodiment, the casing of the container and the filler elements are different reaction products of the solidification of a loose powder of the particles, preferably produced by means of 3DP or SLS. The 3DP method allows for different solutions (e.g., with two print heads), which potentially lead to different reaction products. For example, by printing with water and phosphoric acid and an alpha- TCP, either CDHA (calcium-deficient hydroxyapatite) or DPD (monetite, dicalcium phosphate) can be produced.

In a further embodiment, the casing of the container and the filler elements are the reaction product of a hydraulic cement after its hardening, preferably produced by 3DP.

In yet another embodiment, the casing of the container and the filler elements are the melting product of the composite of a ceramic powder in an SLS process.

In another embodiment, the solidification is based on the reaction of one or more calcium phosphates or calcium sulfates with an aqueous solution.

In another embodiment, the calcium phosphate is the alpha-TCP, beta-TCP, hydroxyapatite, TetCP, or a mixture thereof.

In yet another embodiment, the final product contains DCPD, DCP or a mixture thereof.

In a further embodiment, the solidification takes place due to the reaction of
a) a powder mixture of MCP ($Ca(H_2PO_4)_2$) or MCPM ($Ca(H_2PO_4)_2.H_2O$) or a mixture thereof with
b) one or more of the following substances:
beta-TCP ($Ca_3(PO_4)_2$) or alpha-TCP ($Ca_3(PO_4)_2$) or hydroxyapatite ($Ca_5(PO_4)_3OH$) or calcium-deficient hydroxyapatite ($Ca_{10-x}(HPO_4)_x(PO_4)_{6-x}(OH)_{2-x}$, with $0 \leq x \leq 1$) or tetra calcium phosphate ($Ca_4(PO_4)_2O$), and
c) an aqueous solution or pure water.

Additives to the aqueous liquid to be sprayed by the print head onto the powder bed are acids, hydrogels, alcohols, fats and surfactants. This provides the advantage that the acid required for the solidification reaction is made possible by the MCPM cement reaction with pure water. In doing so, significantly higher mechanical properties are obtained, since it is not the capillary forces that determine the local cement reaction rather a more homogeneous reaction is made possible by the powder layer and thereby a better connection between the individual layers of powder can be achieved.

In another embodiment, the porosity of the filling of the container defined by the filler elements is in the range of 1 to 70%, preferably 20 to 30%. This provides the advantage that the porosity present between the filler elements favors the formation of cells and blood vessels.

In another embodiment the filling elements have pores with an average diameter 1 µm to 50 µm.

In yet another embodiment, the casing also has any arbitrary, even non-rotationally symmetrical form, but the casing is formed preferably rotationally symmetrical.

In another embodiment, the casing has a thickness $d > D_Z$.

In another embodiment, the bone substitute comprises a plurality of interconnected containers, which are arranged side by side or one above the other.

In another embodiment, the bone substitute has, in addition to the plurality of filler elements which are not connected to one another, a number of interconnected filler elements.

In yet another embodiment, the casing has one or more column-like protrusions projecting into the interior of the container.

In a further embodiment of the container in the interior has one or more transverse beams, which are connected to the casing with both their ends.

In a specific embodiment of the method, the layers produced by the 3DP method or the SLS method have a thickness of 10 µm to 250 µm, preferably 30 µm-100 µm.

In a further embodiment of the method, the particles of the hydraulic cement forming the powder consist of MCP and MCPM and TCP and are hardened solely by means of water or aqueous solution. This provides the advantage that, unlike with other calcium phosphates, no phosphoric acid is necessary. Thus, the 3DP print heads (which are usually not designed for acids) are not only protected, but a high quality is made possible because the print head operates reproducibly. Furthermore, in this manner, the calcium/phosphate ratio can be accurately controlled.

In another embodiment of the method, the loose particles left behind inside the container by the 3DP method or the SLS method are removed through least one window from the container by applying one of the following techniques: vacuum, rinsing with a medium in an ultrasonic bath or vibration.

This provides the advantage that the remaining particles of the powder which are not connected to one another form a kind of support function even for overhanging and nested geometries of the container and the filler elements in the 3DP and SLS methods. This is a crucial advantage over other rapid prototyping methods. Thus, the invention overcomes the disadvantage that the remaining particles must be removed. In this case the small movements of the filler elements and the resulting time-dependent deflection and turbulence of the air blown in enable depowdering even complex geometries in the interior of the casing.

A preferred use of the bone substitute is the in vivo colonization with body cells or in vitro culture of cell tissues.

Another preferred use of the bone substitute is the in vitro colonization of bone or cartilage cells.

Preferably, the bone substitute is used for filling or bridging of defects or cavities in bone. The invention and further developments of the invention are explained in more detail below by means of partly diagrammatic representations of several exemplary embodiments.

Figure 1:
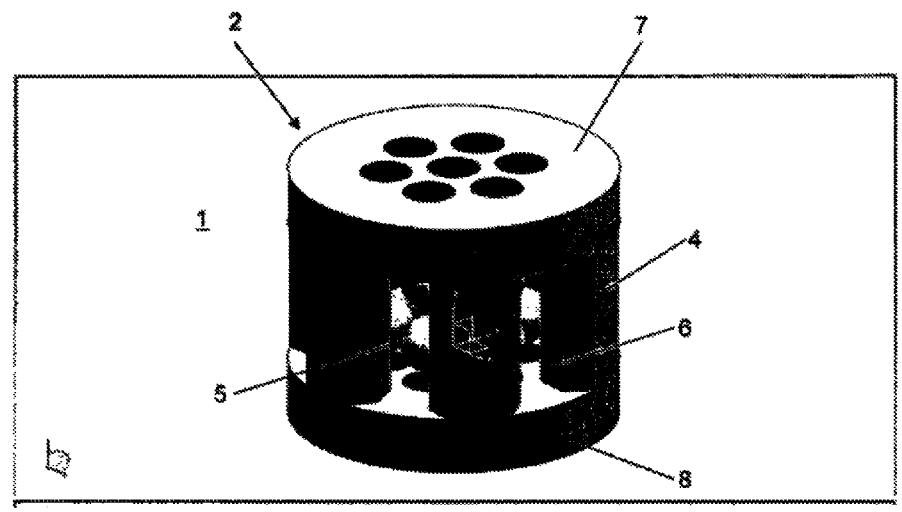
FIG. 1 shows a perspective view of an embodiment of the bone substitute according to the invention.
Figure 2:
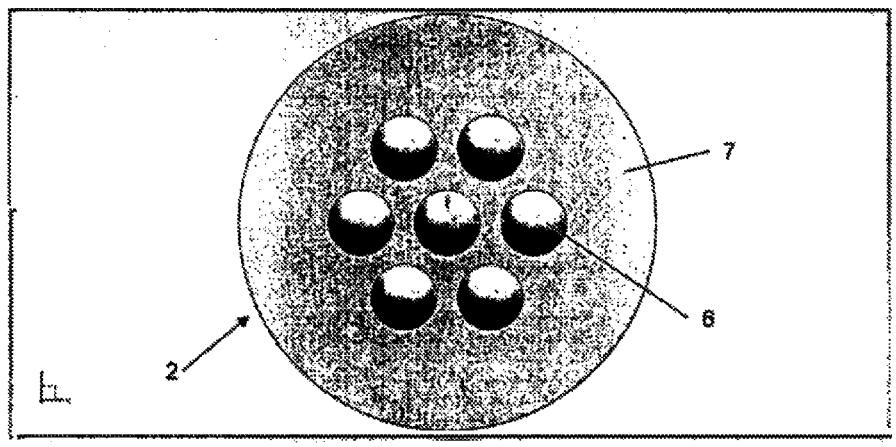
FIG. 2 shows a plan view onto the embodiment of the bone substitute according to the invention shown in FIG. 1.
Figure 3:
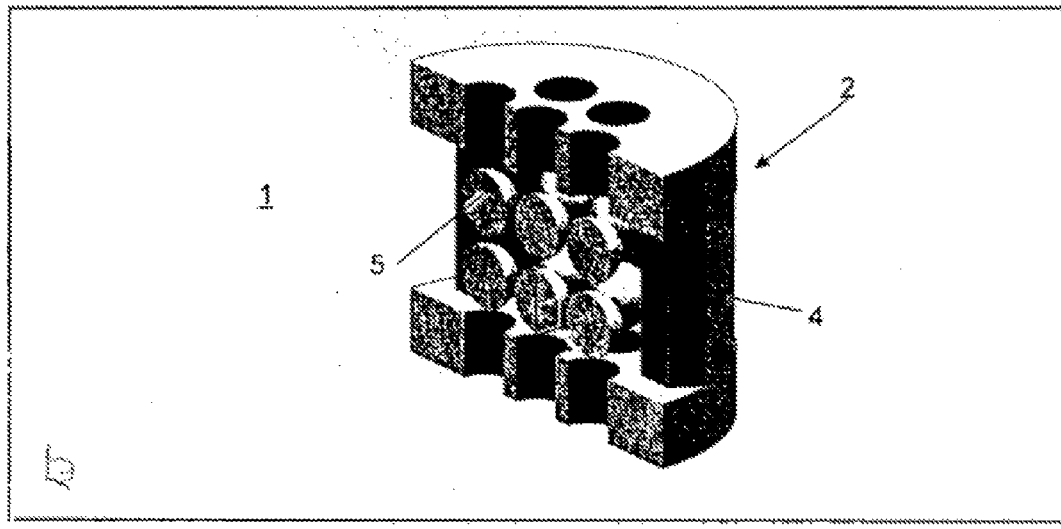
FIG. 3 shows a longitudinal section through the embodiment of the bone substitute according to the invention shown in FIG. 1.
Figure 4:
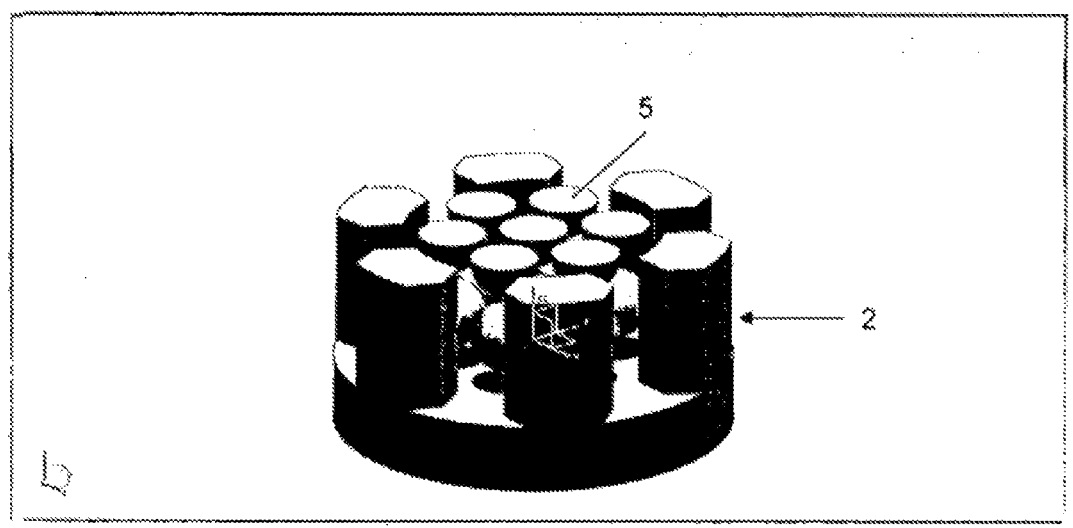
FIG. 4 shows a cross-section through the embodiment of the bone substitute according to the invention shown in FIG. 1.
Figure 5:
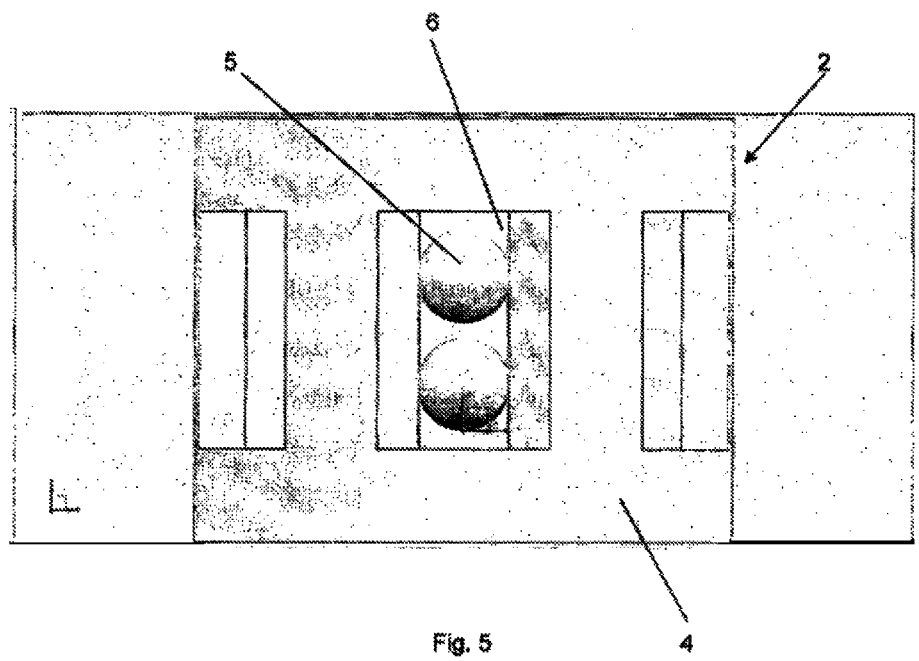
FIG. 5 shows a side view of the embodiment of the bone substitute according to the invention shown in FIG. 1.

FIGS. 1 to 5 show an embodiment of the bone substitute according to the invention 1 which essentially comprises a container 2 and a plurality of filler elements 5 which are enclosed in the container 2. The dimensions of the individual filler elements 5 are defined by their longest enveloping circular cylinder of diameter $D_Z$. The filler elements 5 consist of interconnected particles with an average diameter $D_P$ of at least 1 µm. The diameter $D_Z$ of the longest circular cylinder enveloping a filler element 5 is larger than 200 µm.

The bone substitute 1 may comprise a plurality of interconnected containers 2, which are arranged side by side or one above the other. Furthermore, the bone substitute 1, may comprise, in addition to the plurality of filler elements 5 which are not connected to one another, a number of interconnected filler elements 5.

The container 2 comprises a porous casing 4 which is at least partly provided with openings (not shown), which may have any shape but preferably is formed rotationally symmetrically (e.g., a hollow cylinder). The container 2 further has a container bottom 7, and a container top 8, wherein the container bottom 7 and the container top 8 may also be designed to be porous and at least partly with openings (not shown). The openings of the casing 4, of the container bottom 7 and of the container top 8 are interconnected pores or channels with an average diameter $D_M$, which is smaller than $D_Z$. Furthermore, the container 2 comprises a plurality of windows 6 passing through the casing 4, which are so dimensioned that no filler element 5 passes through one of the windows 6. For this purpose, the windows 6 have a smallest dimension $D_F$ governed by the formula $D_Z > D_F > D_P$. The diameter $D_F$ of the windows 6 is larger than about 50 μm.

Figure 6:
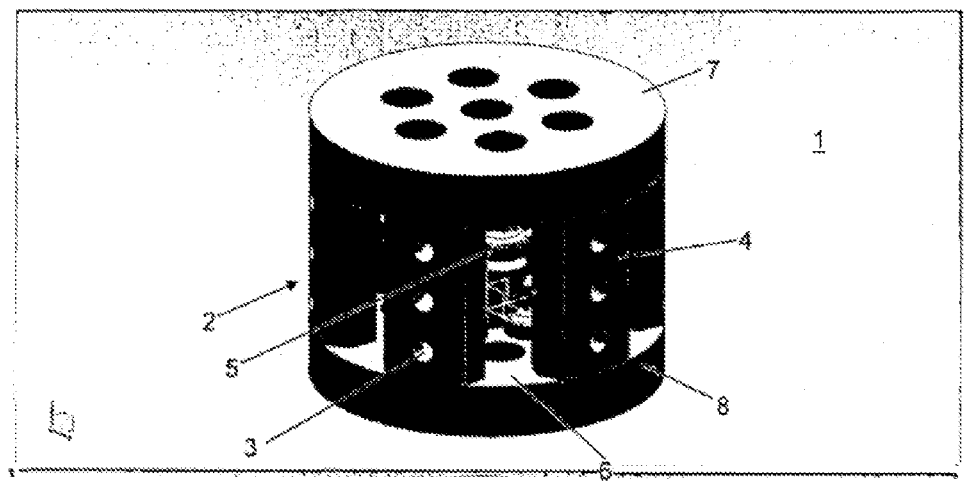
FIG. 6 shows a perspective view of a further embodiment of the bone substitute according to the invention.
Figure 8:
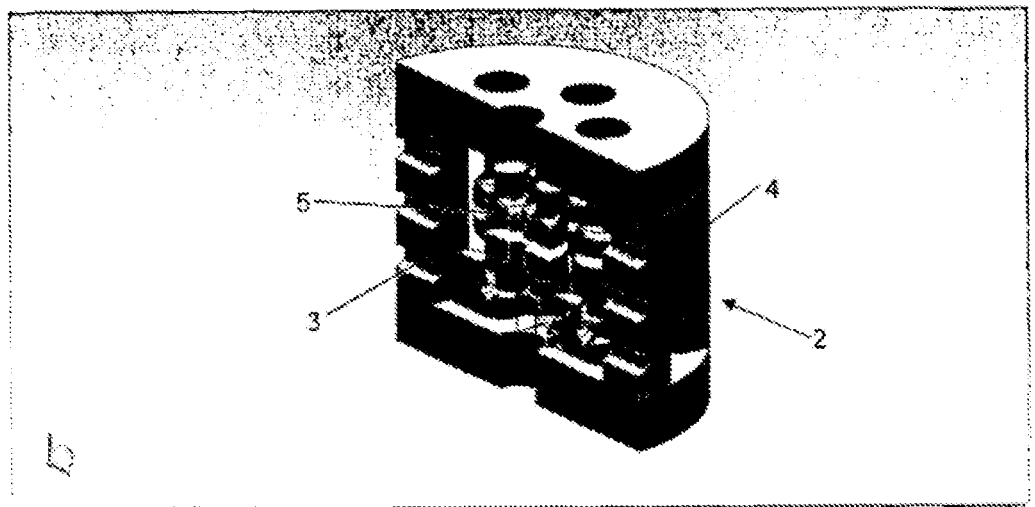
FIG. 8 shows a longitudinal section through the embodiments of the bone substitute according to the invention shown in FIG. 6.
Figure 9:
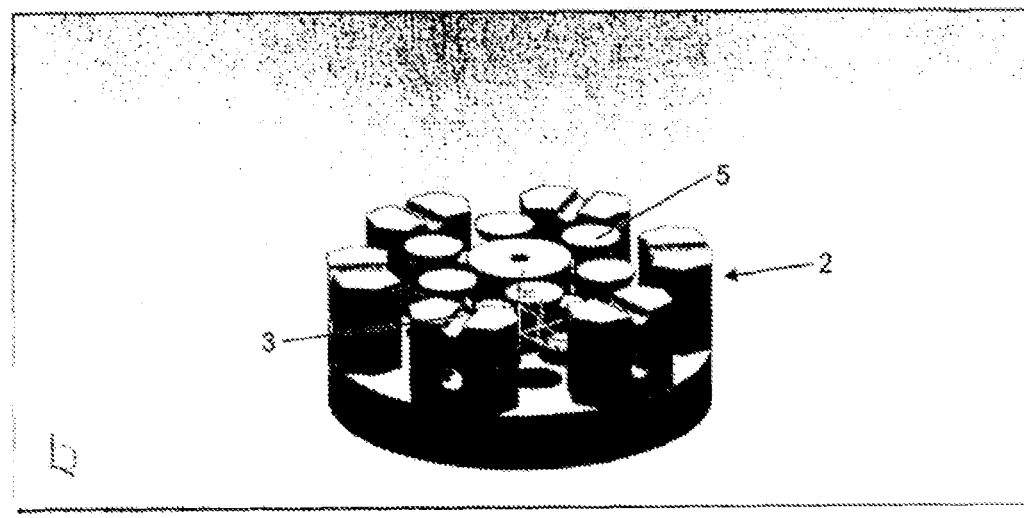
FIG. 9 shows a cross section through the embodiment of the bone substitute according to the invention shown in FIG. 6.
Figure 10:
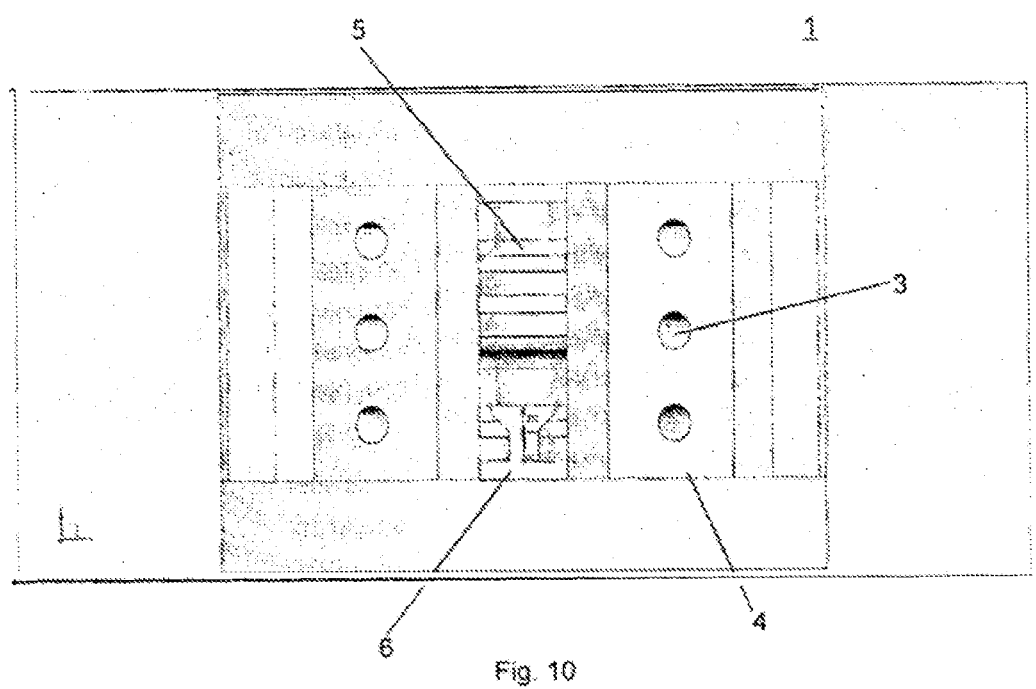
FIG. 10 shows a side view of the embodiment of the bone substitute according to the invention shown in FIG. 6.

Furthermore, the casing 4 may additionally comprise several passages 3 in addition to the openings and the windows 6 (FIGS. 6 and 8 to 10), the diameter $D_D$ of which corresponds at least to the average diameter $D_P$ of the particles forming the filler elements 5 to enable removal of the loose powder, but ideally is larger than 30 μm (angiogenesis). The casing 4 may comprise interparticle and intercrystalline interstices, which have an average diameter in the range of 0.1 $D_P$ to 0.5 $D_P$, wherein the average diameter is between 1 and 50 μm. The thickness d of the casing 4 may be smaller than the diameter $D_Z$ of the longest circular cylinders enveloping the filler elements 5. The casing 4 may have one or more column-like protrusions projecting into the interior of the container 2. In addition or alternatively, the container 2 can have one or more transverse beams, which are connected to the casing with both their ends. The porosity of the filling of the container 2 defined by filler elements 5 is in the range of 1 to 70%. The filler elements 5 are formed, for example, but not limited to, spherically and can have pores with an average diameter of 1 to 50 pm μm.

In addition to the conventional production methods, so-called SFF methods (Solid Free Form Fabrication) are known for producing bone substitute materials. In these so-called SFF methods the geometry is freely definable.

The present invention relates primarily to an application using the powder-based 3DP method (Three-Dimensional Printing) but also directly applicable to other powder-based SFF methods such as SLS (Selective Laser Sintering).

In the 3DP method, so-called 3D printers are used which include machines that build up three-dimensional work pieces. The work pieces are usually built under computer control from one or more liquid or powdered materials according to predetermined dimensions and shapes which can be defined by the CAD methods. The 3DP method is an additive method, wherein a work piece is produced by successively forming layers of material. In addition, physical or chemical hardening processes take place when building the work piece. For producing the work piece, the dimensions and shape are read by the machine and then the individual layers of liquid, powder, or plate-like material are successively deposited so that a work piece made of a series of cross-sectional layers is formed. To produce the work piece, these layers are automatically connected or fused together.

The SLS method is also an additive method, wherein three-dimensional structures are produced from a powdered starting material by sintering. The work piece is also built up layer by layer, wherein small particles of plastic, metal or ceramic are melted by means of high energy lasers (carbon dioxide laser). The material is selectively melted on the surface of a powder bed, so that a solid cross-sectional layer of the work piece is formed after hardening of the molten material. After a layer is complete, the powder bed is lowered by one layer thickness and a new layer of material is applied to the surface of the lowered powder bed. The process is repeated until the work piece is completed.

In one embodiment of the method according to the invention for producing the bone substitute 1, the casing 4 of the container 2 and the plurality of filler elements 5 are produced simultaneously in layers by means of 3DP or SLS methods. The layers produced by the 3DP or SLS method can have a thickness of 10 μm to 250 μm, preferably 30 μm-10 μm. Furthermore, the particles of the hydraulic cement forming the powder may consist of MCPM (Ca$(H_2PO_4)_2.H_2O$) or MCP (Ca$(H_2PO_4)_2$) and TCP and may be hardened solely by means of an aqueous solution or water. The loose particles left behind inside the container by the 3DP method or the SLS method and which have not hardened can be removed through at least one window 6 from the container 2 by applying one of the following techniques: vacuum, rinsing with a medium in an ultrasonic bath or vibration.

Below, for the sake of simplicity, only the 3DP method is mentioned. However, this implies also alternative methods. Although the geometry is freely definable in these methods, undercut and overhanging and nested geometries must be supported, since the structure is built in layers. This in turn requires a later removal of these supports. In the case of 3DP and SLS the support function is taken over by loose powder, which has to be removed again later (depowdering). Nowadays, this is done normally with air pressure in the case of parts produced by 3DP and SLS. For this purpose, an airbrush nozzle is used, blowing filtered compressed air onto the bone substitute according to the invention. This will free from the outside the bone substitute produced according to the invention step by step from loose particles of the powder used. In particular, inside the bone substitute produced according to the invention this is done only with difficulties. Therefore, in SFF methods, the geometrical freedom in the interior is limited by the freedom of the removal of the free powder. If the remaining unhardened powder cannot be removed, the geometry is lost. In practice, this limits severely the choice of the geometry especially in the interior of a body. Typically, large channels have to be built, enabling a "depowdering". The present invention focuses heavily on a better solution for the "depowdering" which thereby makes possible a new type of bone substitute. Moreover, this method allows for efficient and economical production.

Another inventive novelty relates to the composition of the powder. The prior art in 3DP for bone substitute is the following: An acid is applied onto the powder bed by means of a print head, whereby the ceramic powder particles are joined locally by means of a precipitation reaction. A novel method by mixing the ceramic particles (e.g., CaP calcium phosphates) with the particles which on contact with water form acid (e.g., MCP mono-calcium phosphate) allows printing with water. In addition to precise adjustment of the calcium/phosphate ratio this offers other advantages, described below in terms of the mechanical properties and the production method. One way to improve the mechanical properties of bone substitute according to the invention further lies in so-called "post-hardening" steps, i.e., the bone substitute produced according to the invention is, for example, enhanced by immersion in an acid bath, by thermal post-treatment, e.g., by sintering, or by chemical post-treatment (infiltration). In the case of the novel printing with a water-based and acid-free solution on a CaP/MCP powder bed, therefore, a new and completely unproblematic "post-hardening" is possible by solidifying the bone substitute at controlled or saturated humidity or by direct contact with water (with capillary soaking, immersing or spraying) by subsequent crystal formation.

The casing 4 of the container 2 and the filler elements 5 may be the reaction product of the solidification of a loose powder of the particles and are produced by means of 3DP or SLS. Examples include a) solidification by crystal formation or polymerization (e.g., sugar or salt powder+water from the print head or as a further alternative, any powder+salt/sugar/polymer solution from the print head (e.g., sugar/CaP powder bed is sprayed locally with water droplets (from the print head via 3DP). Interlocking of the sugar crystals forms a matrix which holds together the CaP particles. Subsequent steps could include a further composite of CaP or washing out of the sugar crystals; b) solidification by capillary forces: drying and interlocking of the surface of a powder; c) solidification by gelation (e.g. alginate+$Ca^{2+}$ ions=gel); d) solidification by cooling (e.g., a liquid medium is printed on a powder and solidifies by cooling); or e) solidification by sintering or melting and cooling (SLS or SLM (Selective Laser Melting) method.

Alternatively, the casing 4 of the container 2 and the filler elements 5 may be the reaction product of a hydraulic cement after its hardening, preferably produced by 3DP, but also the reaction product of the composite of a, e.g., ceramic and polymer powder mixture in a SLS process.

Furthermore, the solidification may be based on the reaction of one or more calcium phosphates, or calcium sulfates with an aqueous solution. Here, the calcium phosphate may be alpha-TCP, beta-TCP, hydroxyapatite, TetCP, or a mixture thereof.

In alternative embodiments the solidification can take place due to the reaction of a) a powder mixture of MCP ($Ca(H_2PO_4)_2$) or MCPM ($Ca(H_2PO_4)_2 \cdot H_2O$) or a mixture thereof with b) one or more of the following substances: beta-TCP ($Ca_3(PO_4)_2$) or alpha-TCP ($Ca_3(PO_4)_2$) or hydroxyapatite ($Ca_5(PO_4)_3OH$) or calcium-deficient hydroxyapatite ($Ca_{10-x}(HPO_4)_x(PO_4)_{6-x}(OH)_{2-x}$, with $0 \leq x \leq 1$) or tetra calcium phosphate ($Ca_4(PO_4)_2O$), and c) an aqueous solution or pure water.

Figure 7:
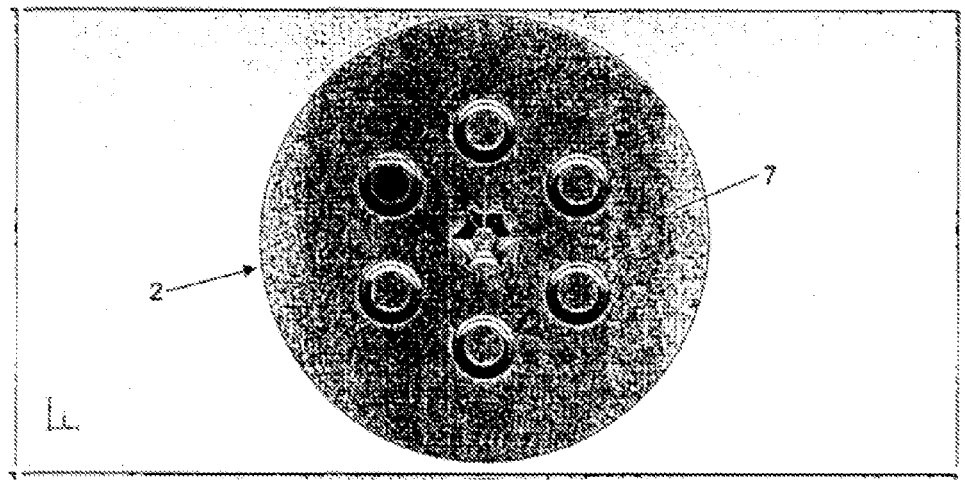
FIG. 7 is a plan view of the embodiments of the bone substitute according to the invention shown in FIG. 6.

The embodiment shown in FIGS. 6 to 10 of the bone substitute 1 according to the invention differs from the embodiment described in FIG. 1-5 only in that that the filler elements 5 are T-shaped or mushroom-shaped. Here, the filler elements 5 may comprise two essentially circular cylindrical portion, of which a respective first portion having a larger diameter than the adjoining second portion. Differently configured embodiments of the filler elements 5 are also possible and can be combined at will.

Although, as described above, various embodiments of the present invention are present, they are to be understood that the various features can be used both individually and in any combination.

This invention is therefore not just limited to the aforementioned particularly preferred embodiments.

The invention claimed is:

1. A bone substitute comprising:
    a container made of a porous casing which is at least partly provided with openings; and
    a plurality of filler elements which are not connected to one another or to the container and which are fully enclosed within an interior of the container such that the plurality of filler elements cannot escape from the container;
    wherein individual filler elements are formed of interconnected particles, said particles having an average diameter $D_P$,
    wherein the openings of the casing are interconnected pores or channels having an average diameter of $D_M$,
    wherein the container containing the plurality of filler elements is a bone substitute,
    wherein the individual filler elements have a diameter $D_Z$, said diameter being defined by a longest enveloping circular cylinder,
    wherein the container comprises at least one window passing through the casing, and
    wherein the at least one window has a smallest diameter $D_F$ which is governed by formula $D_Z > D_F > D_P$.

2. The bone substitute according to claim 1, wherein the average diameter $D_P$ of the particles is between 1 μm and 250 μm.

3. The bone substitute according to claim 1, wherein the average diameter $D_M$ of the pores or channels is less than $D_Z$.

4. The bone substitute according to claim 1, wherein the diameter $D_Z$ is larger than 200 μm.

5. The bone substitute according to claim 1, wherein the diameter $D_F$ is larger than 50 μm.

6. The bone substitute according to claim 1, wherein the filler elements and the casing are produced in one operation by means of a three-dimensional printing method or a selective laser-sintering process.

7. The bone substitute according to claim 1, wherein the filler elements are spaced apart from one another, and wherein a minimal distance between the filler elements is larger than 50 μm.

8. The bone substitute according to claim 1, wherein the casing contains, in addition to the openings and the at least one window, a number of passages having a diameter $D_D$ which is at least equal in size to $D_P$ and is at least 30 μm.

9. The bone substitute according to claim 1, wherein the casing has interparticle and intercrystalline interstices with an average diameter which is in a range of 0.1 $D_P$ to 0.5 $D_P$, and is from 1 to 50 μm.

10. The bone substitute according to claim 1, wherein the casing of the container and the filler elements are a reaction product of a solidification of a loose powder of the particles.

11. The bone substitute according to claim 10, wherein the casing of the container and the filler elements are a reaction product of a hydraulic cement after hardening.

12. The bone substitute according to claim 10, wherein the casing of the container and the filler elements are a melting product of a composite of a ceramic powder in a selective laser-sintering process.

13. The bone substitute according to claim 10, wherein the solidification is based on a reaction of one or more calcium phosphates or calcium sulfates with an aqueous solution.

14. The bone substitute according to claim 13, wherein the one or more calcium phosphates is selected from the group consisting of alpha-TCP, beta-TCP, hydroxyapatite, TetCP, and mixtures thereof.

15. The bone substitute according to claim 10, wherein solidification takes place due to the reaction of:
    a) a powder mixture of MCP ($Ca(H_2PO_4)_2$) or MCPM ($Ca(H_2PO_4)_2 \cdot H_2O$) or both;

b) one or more of
 beta-TCP ($Ca_3(PO_4)_2$),
 alpha-TCP ($Ca_3(PO_4)_2$),
 hydroxyapatite ($Ca_5(PO_4)_3OH$),
 calcium-deficient hydroxyapatite ($Ca_{10-x}(HPO_4)_x(PO_4)_{6-x}(OH)_{2-x}$, with $0 \leq x \leq 1$), and
 tetra calcium phosphate ($Ca_4(PO_4)_2O$); and
c) an aqueous solution or pure water.

16. The bone substitute according to claim 1, wherein the casing of the container and the filler elements are different reaction products of a solidification of a loose powder of the particles.

17. The bone substitute according to claim 1, the bone substitute contains DCPD, DCP or a mixture thereof.

18. The bone substitute according to claim 1, wherein a porosity of a filling of the container defined by the filler elements is in a range of 1 to 70%.

19. The bone substitute according to claim 1, wherein the filler elements have pores with an average diameter from 1 µm to 50 µm.

20. The bone substitute according to claim 1, wherein the casing is rotationally symmetrical.

21. The bone substitute according to claim 1, wherein the casing has a thickness $d > D_Z$.

22. The bone substitute according to claim 1, wherein the bone substitute comprises a plurality of interconnected containers, which are arranged side by side or one above another.

23. The bone substitute according to claim 1, wherein the casing has one or more column-like protrusions projecting into the interior of the container.

24. The bone substitute according to claim 23, wherein the container in the interior has one or more transverse beams, which are connected to the casing at both ends.

25. A method for producing a bone substitute according to claim 1, wherein the casing of the container and the plurality of filler elements are produced simultaneously in layers by three-dimensional printing, selective laser-sintering or selective laser-sintering with ceramic.

26. The method according to claim 25, wherein layers produced by three-dimensional printing or by selective laser-sintering have a thickness of 10 µm to 250 µm.

27. The method of claim 25, wherein the filler elements are a reaction product of a hydraulic cement after hardening, and the hydraulic cement is formed of a powder consisting of MCP and MCPM and TCP and is hardened solely by means of water or an aqueous solution.

28. The method according to claim 25, wherein loose particles left behind inside the container by three-dimensional printing or by selective laser-sintering are removed through the at least one window from the container by vacuum, by rinsing with a medium in an ultrasonic bath, or by vibration.

29. The bone substitute according to claim 1, wherein there are no toxic components present in the bone substitute that would make it unsuitable for in vivo colonization with body cells or in vitro culture of cell tissues.

* * * * *